US00PP13657P2

(12) United States Plant Patent
Koppe

(10) Patent No.: US PP13,657 P2
(45) Date of Patent: Mar. 11, 2003

(54) BEGONIA PLANT NAMED 'BINOS'

(75) Inventor: Lubbertus H. Koppe, Ermelo (NL)

(73) Assignee: Koppe Veredeling B.V., Ermelo (NL)

( * ) Notice: Subject to any disclaimer, the term of this patent is extended or adjusted under 35 U.S.C. 154(b) by 0 days.

(21) Appl. No.: 10/077,378

(22) Filed: Feb. 15, 2002

(51) Int. Cl.[7] ..... A01H 5/00

(52) U.S. Cl. ..... Plt./348

(58) Field of Search ..... Plt./348, 349

*Primary Examiner*—Bruce R. Campell
*Assistant Examiner*—Jane Hwu
(74) *Attorney, Agent, or Firm*—C. A. Wealy

(57) ABSTRACT

A new and distinct cultivar of Begonia plant named 'Binos', characterized by its upright and mounded plant habit; double flowers that are light pinkish red in color and held above the foliage; and excellent postproduction longevity.

1 Drawing Sheet

BOTANICAL CLASSIFICATION/CULTIVAR DESIGNATION

*Begonia×hybrida* cultivar cultivar Binos.

BACKGROUND OF THE INVENTION

The present Invention relates to a new and distinct cultivar of Begonia plant, botanically known as *Begonia×hiemalis*, commercially known as Elatior Begonia, and hereinafter referred to by the name 'Binos'.

The new Begonia was discovered by the Inventor in a controlled environment in Ermelo, The Netherlands, in October, 1999, as a naturally-occurring whole plant mutation of *Begonia×hiemalis* 'Bastos', not patented. The new Begonia was observed as a single plant in a group of flowering plants of the parent cultivar. The selection of this plant was based on its flower coloration.

Asexual reproduction of the new Begonia by cuttings taken in a controlled environment in Ermelo, The Netherlands, has shown that the unique features of this new Begonia are stable and reproduced true to type in successive generations.

SUMMARY OF THE INVENTION

The cultivar 'Binos' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Binos'. These characteristics in combination distinguish 'Binos' as a new and distinct Begonia:

1. Upright and mounded plant habit.
2. Double flowers that are light pinkish red in color and held above the foliage.
3. Excellent postproduction longevity.

Plants of the new cultivar differ from plants of the parent, the cultivar Bastos, primarily in flower color as plants of the cultivar Bastos have darker colored flowers than plants of the cultivar Binos.

Plants of the new cultivar differ primarily from plants of the cultivar Bellona, disclosed in U.S. Plant Pat. No. 10,476, in flower color as plants of the cultivar Bellona have darker colored flowers than plants of the cultivar Binos.

BRIEF DESCRIPTION OF THE PHOTOGRAPH

The accompanying colored photograph illustrates the overall appearance of the new Begonia, showing the colors as true as it is reasonably possible to obtain in colored reproductions of this type. Colors in the photograph may differ slightly from the color values cited in the detailed botanical description which accurately describe the colors of the new Begonia. The photograph comprises a side perspective view of a typical flowering plant of 'Binos'.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Ermelo, The Netherlands, under commercial practice in a glass-covered greenhouse. Average day and night temperatures were about 20° C. during the first three to four weeks then lowered to an average day and night temperature of 19° C. until flowering. Four weeks after planting rooted cuttings in 12-cm containers, one week of long nyctoperiods of 16 hours was given followed by short nyctoperiods of eight hours until flowering. Plants used for the photographs and the description were about four months old. Measurements and numerical values represent averages for typical flowering plants.

Botanical classification: *Begonia×hiemalis* cultivar Binos.
Commercial classification: Elatior Begonia.
Parentage: Naturally-occurring whole plant mutation of *Begonia×hiemalis* cultivar Bastos, not patented.
Propagation:
- *Type.*—Cuttings.
- *Time to develop roots.*—About 40 days at temperatures of 20 to 22° C.
- *Root description.*—Fine, fibrous, well-branched and spreading. Plants of the new Begonia have not been observed to form tubers.

Plant description:
- *Plant form.*—Upright and mounded plant habit, inverted triangle; freely branching with good stem and stem base strength. Flowers are double and abundant. Plants flower continuously.

*Growth habit.*—Moderate growth rate, vigorous. Suitable for 12 to 15-cm containers. Under optimal environmental and cultural conditions, usually about four months are required to produce proportional 13-cm potted plants from cuttings. Vegetative shoots are formed at basal nodes and flowering shoots are formed at upper nodes.

*Plant height.*—About 24.5 cm.

*Plant width.*—About 40 cm.

*Leaves.*—Arrangement: Simple, alternate. Young leaves, length: About 4.5 cm. Young leaves, width: About 5.9 cm. Fully expanded leaves, length: About 9 cm. Fully expanded leaves, width: About 10 cm. Shape: Asymmetrical, more or less reniform. Apex: Acuminate. Base: Cordate. Margin: Doubly serrate. Texture: Glabrous, smooth. Venation pattern: Palmate. Color: Young leaves, upper surface: Darker than 147A. Young leaves, lower surface: 148C. Fully expanded leaves, upper surface: Much darker than 147A. Fully expanded leaves, lower surface: 148C. Venation, upper and lower surfaces: 145B. Petiole length: About 5.75 cm. Petiole texture: Slightly pubescent. Petiole color: 180C.

Flower decription:

*Flowering habit.*—Double flowers with numerous tepals arranged in axillary cymes. Usually 9 to 12 flowers per cyme. Many cymes in flower simultaneously. Flowers positioned above the foliage. Flowering continuous.

*Natural flowering season.*—Pants will flower year around regardless of nyctoperiod, however plants flower earlier and more abundantly from mid-February until November in the Northern Hemisphere.

*Flowers.*—Shape: Rounded. Diameter: About 6.75 cm. Depth (height): About 2.8 cm.

*Flower buds.*—Length: About 1.7 cm. Diameter: About 1.4 cm. Color: 145C, towards margin, 41D.

*Tepals.*—Arrangement: Rosette. Shape: Rounded flabellate. Apex: Rounded. Margin, outer and inner tepals: Slightly crenate. Quantity per flower: Usually about 36 per flower. Size: Outer tepals: Length: About 3.5 cm. Width: About 3.7 cm. Inner tepals: Length: About 3 cm. Width: About 3 cm. Texture: Smooth, satiny, glabrous. Color: When opening, upper and lower surfaces: 41B. Fully opened, upper surface: 41B; flower color fading to 41C to 41D with subsequent development. Fully opened, lower surface: 41C.

*Flower bracts.*—Arrangement: Two, opposite. Shape: Broadly cordate. Apex: Apiculate. Margin: Serrate. Texture: Glabrous. Color, both surfaces: 146C.

*Peduncles.*—Angle: Erect. Length: About 5 cm. Texture: Slightly pubescent. Color: Close to 180C to 180D.

*Pedicels.*—Angle: Erect. Length: About 2.9 cm. Texture: Glabrous. Color: 145B.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease/pest resistance: Resistance to pathogens and pests common to Begonia has not been observed.

It is claimed:

1. A new and distinct cultivar of Begonia plant named 'Binos', as illustrated and described.

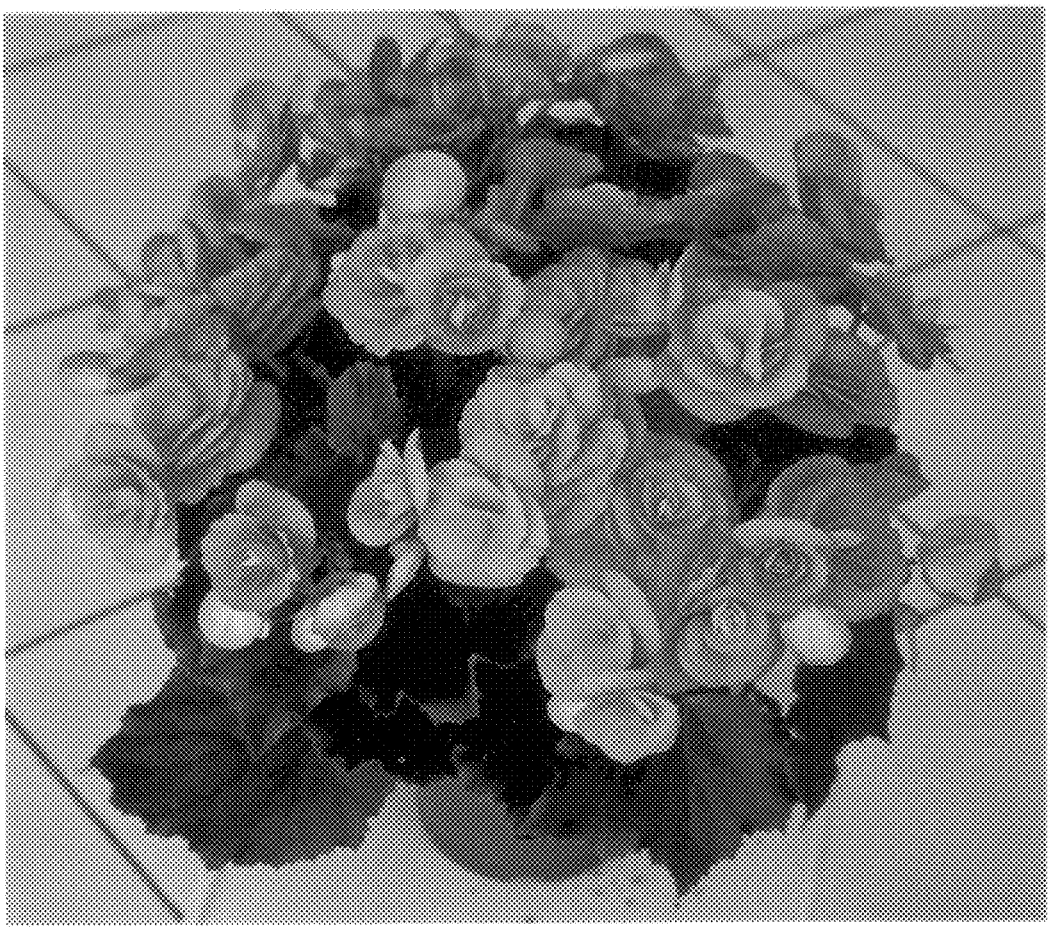

* * * * *